United States Patent [19]

Caterson et al.

[11] Patent Number: 5,374,529

[45] Date of Patent: Dec. 20, 1994

[54] METHODS OF AND COMPOSITIONS FOR DIAGNOSIS, MONITORING AND TREATING THE EARLY STAGES OF OSTEOARTHRITIS

[76] Inventors: Bruce Caterson, Apt. J2, Carolina Apts., 401 Hwy. 54 Bypass, Carrboro, N.C. 27510; Timothy E. Hardingham, 55 Lambton Road, London SW20, England

[21] Appl. No.: 789,404

[22] Filed: Nov. 1, 1991

Related U.S. Application Data

[63] Continuation of Ser. No. 261,148, Oct. 24, 1988, abandoned.

[51] Int. Cl.$^5$ ............................................. G01N 33/53
[52] U.S. Cl. ................................ 435/7.1; 435/7.9; 435/7.92; 435/70.21; 435/240.27; 436/501; 436/503; 436/530; 436/531; 436/548; 436/811; 530/388.1
[58] Field of Search .................. 435/7.9, 7.92, 240.27, 435/7.1, 70.21; 436/503, 501, 548, 530, 531, 811; 530/388.1

[56] References Cited

U.S. PATENT DOCUMENTS 4,704,356  11/1987  Thonar ................................ 436/7.92
4,778,768  10/1988  Heinegard et al. .................. 436/506

OTHER PUBLICATIONS

Rizkalla et al., "Studies of the Articular Cartilage Proteoglycan Aggrecan in Health and Osteoarthritis," *J. Clin. Invest.*, vol. 90 (1992) pp. 2268–2277.

Sorrell et al., *J. Immunol.*, vol. 140, No. 12 (1988), pp. 4263–4270.

Sorrell et al., *J. Cell. Biol.*, vol. 105, p. 298a, Abstract 1681, (1987).

Adams et al., Journal of Rheumatology, vol. 14, pp. 107–109 (1987).

Cox et al., Biochimica et Biophysica Acta, vol. 840(2), pp. 228–234 (1985).

Vasan, N., Biochem. Journal, vol. 187, pp. 781–787 (1980).

Hjertquist et al., Chemical Abstracts, vol. 77:99267s (1972).

Bollet, A. J., Chemical Abstracts, vol. 68:11148j (1968).

S. L. Carney et al., "Electrophoresis of $^{35}$S–Labeled Proteoglycans on Polyacrylamide–Agarose Composite Gels and Their Visualization by Fluorography", *Analytical Biochemistry*, 156, pp. 38–44 (1986).

B. Caterson et al., "Identification of a Monoclonal Antibody that Specifically Recognizes Corneal and Skeletal Keratan Sulfate", *Journal of Biological Chemistry*, 258 (14) pp. 8848–8854 (1983).

B. Caterson et al., "Monoclonal Antibodies as Probes for Elucidating Proteoglycan Structures and Function", *Biology of Proteoglycans*, ed., T. Wright and R. Mecham, Academic Press, N.Y., pp. 1–26 (1987).

B. Caterson et al., "Monoclonal Antibodies Against Cartilage Proteoglycan and Link Protein", Articular Cartilage Biochemistry, ed., K. Kuettner et al., Raven Press, New York, pp. 59–73 (1986).

B. Caterson et al., "Production Characterization of Monoclonal Antibodies Directed Against Connective Tissue Proteoglycans", *Fed. Proc.* 44, pp. 386–393 (1985).

J. E. Christner et al., "Immunological Determinants of Proteoglycans", The Journal of Biological Chemistry, 255, (15) pp. 7102–7105 (1980).

J. R. Couchman et al., "Mapping by Monoclonal Antibody Detection of Glycosaminoglycans in Connective Tissue", *Nature*, 307, pp. 650–652 (1984).

A. L. DeBlas et al., "Detection of Antigens on Nitrocellulose Paper Immunoblots with Monoclonal Antibodies", *Analytical Biochemistry*, 133, pp. 214–219 (1983).

R. W. Farndale et al., "A Direct Spectrophotometric Microassay for Sulfated Glycosaminoglycans in Cartilage Cultures", *Connective Tissue Research*, 9, pp. 247–248 (1982).

M. J. Pond et al., "Experimentally–Induced Osteoarthritis in The Dog", *Annals of the Rheumatic Diseases*, 32, pp. 387–388 (1973).

A. Ratcliffe et al., "Cartilage Proteoglycan Binding Region and Link Protein", *Biochem J.*, 213, pp. 371–378 (1983).

J. M. Sorrel et al., "Immunochemical Characterization and Ultrastructural Localization of Chondroitin Silfates and Keratan Sulfate in Embryonic Chick Bone Marrow", *Cell and Tissue Research*, 252, pp. 523≧531 (1988).

*Primary Examiner*—Esther M. Kepplinger
*Assistant Examiner*—Susan C. Wolski
*Attorney, Agent, or Firm*—James F. Haley, Jr.; Leslie A. McDonell

[57] ABSTRACT

Methods of and compositions for early diagnosis, monitoring and treatment of osteoarthritis using monoclonal antibodies which specifically recognize antigenic determinants on atypical chondroitin sulfate/dermatan sulfate glycosaminoglycan chains in body tissues and fluids, which determinants are markers of osteoarthritis.

1 Claim, 6 Drawing Sheets

FIG. 1

METHODS OF AND COMPOSITIONS FOR DIAGNOSIS, MONITORING AND TREATING THE EARLY STAGES OF OSTEOARTHRITIS

This is a continuation of application Ser. No. 07/261,148, filed Oct. 24, 1988, now abandoned, entitled METHODS OF AND COMPOSITIONS FOR DIAGNOSIS, MONITORING AND TREATING THE EARLY STAGES OF OSTEOARTHRITIS.

FIELD OF THE INVENTION

This invention relates to methods of and compositions for early diagnosis, monitoring and treatment of osteoarthritis using monoclonal antibodies which specifically recognize antigenic determinants on atypical chondroitin sulfate/dermatan sulfate glycosaminoglycan chains of cartilage proteoglycans from humans and animals with osteoarthritis, such atypical chains being markers of osteoarthritis.

BACKGROUND OF THE INVENTION

Osteoarthritis is a degenerative process in joints characterized by functional deterioration, abrasion of articular cartilage, and formation of new bone at and around the joint surfaces. It is estimated to affect approximately 40 million adults in the United States alone. The disease is particularly prevalent in individuals over the age of 55 and with the longevity of the population increasing, it has become a disease of major concern to the medical community.

In humans, osteoarthritis takes years to develop. As the disease progresses, the affected diseased cartilage literally wears away. At the present time, osteoarthritis cannot be diagnosed until quite late in the degenerative process. Current medical treatment therefore consists mainly of trying to reverse the later inflammatory stage of the disease. At this point, it is really too late to stop or reverse the degenerative process.

It has long been acknowledged in the literature that the events leading up to these late inflammatory stages are the most important. Many drug companies have for example given up the idea of treating osteoarthritis with anti-inflammatory drugs and are now trying to discover and develop drugs that will treat the primary lesion or the early stages of the disease. However, assays to monitor the effectiveness of these drugs on the early stages of osteoarthritis are not available. Moreover, diagnosis of the disease in its early stages has also not been possible. Therefore, in a clinical setting, it cannot be determined which patients are affected by the disease in its earliest stages and thus, are candidates for such drugs and therapies.

U.S. Pat. No. 4,704,356 refers to a potential marker for diagnosing osteoarthritis. It employs a quantitative immunoassay for keratan sulfate, which is thought to be elevated in patients with osteoarthritis. This immunoassay is not satisfactory for the diagnosis of osteoarthritis. First, it detects an increased release of a normal tissue component without selectively identifying a pathological process. More importantly, there is still much controversy in the field over whether the initial stages of the degenerative process are associated with an abnormally high or an abnormally low level of keratan sulfate. Finally, the method of the '356 patent is useful only prospectively, i.e., to confirm the presence of osteoarthritis. It has not been used to diagnose or track the disease in its earliest stages.

As a result, clinical assessment of osteoarthritis is hampered by the lack of sound diagnostic criteria and the absence of means to detect and measure the active processes of joint damage. Because the disease is widespread, heterogeneous and slowly progressive, the need for definitive and reliable tests is paramount not only for diagnosis, but also for longitudinal assessment, epidemiology and drug development.

SUMMARY OF THE INVENTION

It is therefore an object of this invention to identify a characteristic marker of an early stage of osteoarthritis. It is a further object of this invention to use this marker to develop methods and compositions for diagnosing, monitoring and treating osteoarthritis.

The present invention accomplishes these objects by demonstrating for the first time that atypical chondroitin sulfate or dermatan sulfate glycosaminoglycan chains of osteoarthritic cartilage proteoglycans are markers for and characterize the early stages of osteoarthritis. We believe that these markers contain subtle structural domains that are atypical to the common chondroitin sulfate or dermatan sulfate glycosaminoglycan chains found in normal mature cartilaginous tissues.

In further embodiments of this invention, monoclonal antibodies that selectively recognize these atypical structures are produced for use in methods of and compositions for the diagnosis of the early stages of osteoarthritis. Another aspect of this invention provides methods of and compositions for the treatment of osteoarthritis using therapeutic drugs linked to the monoclonal antibodies of this invention. In this way the drug is specifically targeted to the diseased versus normal tissue.

Yet another aspect of this invention is the use of these monoclonal antibodies in methods and compositions for monitoring the course of osteoarthritis and determining the effect of treatment thereof. This embodiment is particularly useful in animal models to screen and test for drugs which prevent or treat the earliest stages of osteoarthritis.

DETAILED DESCRIPTION OF THE INVENTION

In order that the invention described herein may be more fully understood, the following detailed description is set forth.

Proteoglycans are major components of the extracellular matrix of cartilage and are responsible for the stiffness and elasticity of the tissue. Cartilage proteoglycans are complex macromolecules in which many glycosaminoglycan chains and oligosaccharides are linked to an extended protein core. Five separate domains have been identified in the cartilage proteoglycan protein core: a highly folded globular region that forms the hyaluronate-binding site, a second globular domain of unknown function that shares sequence homology with the hyaluronate binding region, a short extended keratan sulfate-rich region, a long extended chondroitin sulfate-bearing region, and a C-terminal globular domain that may possess lectin-like properties. Dermatan sulfate differs from chondroitin sulfate only in the presence of a variable portion of iduronate residues in the place of glucuronate residues.

In this description and application, atypical chondroitin sulfate/dermatan sulfates are defined as chains that have subtle structural domains characteristic of osteoarthritis (but not normal cartilage tissue). Among these atypical chondroitin sulfate/dermatan sulfate chains are those that are specifically recognized by monoclonal antibodies 5/6/3-B-3 (human, dog and guinea pig cartilage proteoglycans) or 8/25/7-D-4 (dog and guinea pig cartilage proteoglycans). Other such atypical chondroitin sulfate/dermatan sulfate chains are those specifically recognized by the other monoclonal antibodies of this invention.

As described herein, our discovery and identification of these atypical chondroitin sulfate/dermatan sulfate chains and our recognition that they serve as specific markers for osteoarthritis have permitted us to develop methods of and compositions for diagnosing early stages of osteoarthritis in mammals. Our discovery of these atypical chondroitin sulfate/dermatan sulfate chains has also permitted us to develop methods of and compositions for monitoring the course of osteoarthritis in mammals. Such monitoring is especially important in drug development and screening, and in following the course of a selected therapy in clinical applications. For example, it is an important aspect of this invention that drug companies and other researchers may use the methods and compositions of this invention in animal models to search for and test drugs which prevent or treat the early stages of osteoarthritis.

The compositions that are useful in the monitoring and diagnostic embodiments of this invention are characterized by monoclonal antibodies that are selectable using the following protocol: monoclonal antibodies are produced against the proteoglycans of cartilage extracts from a mammal suffering from osteoarthritis and screened for those (1) that selectively recognize proteoglycans of cartilage extracts from a mammal suffering from osteoarthritis (preferably the same mammal from which the antigen used to raise the antibody is derived), (2) that do not recognize or that recognize to a significantly lesser extent than in screen (1) proteoglycans of cartilage extracts from a mammal not suffering from osteoarthritis (preferably the same mammal as used in the first screening and more preferably the same mammal as used to derive the antigen and in the first screening) and (3) that do not recognize proteoglycans of cartilage extracts from a mammal suffering from osteoarthritis, from which the chondroitin sulfate/dermatan sulfate chains have been completely removed by enzymatic or chemical treatment (again most preferably the same mammal from which the antigen used in raising the antibody is derived and also the same mammal used in the first and second screening).

In screen (1) and (2) above it is important that proteoglycans of cartilage extracts from a mammal suffering or not suffering from osteoarthritis are not treated with chondroitinase, hyaluronidase or other enzymes that may cleave or otherwise modify the chain structure. Chondroitin sulfate/dermatan sulfate chains may be completely removed by enzymatic or chemical methods such as treatment with alkaline borohydride, anhydrous hydrogen fluoride or trifluoro methane sulfonic acid. Screen (3) serves to eliminate those antibodies recognizing proteoglycan antigens that are not part of chondroitin sulfate/dermatan sulfate chain structures.

Among the antibodies selectable by this defined protocol are monoclonal antibodies 5/6/3-B-3, 8/25/7-D-4 and antibodies which are immunologically crossreactive with them (immunologically crossreactive being defined as the ability to bind to substantially the same epitopes on atypical chondroitin sulfate/dermatan sulfate chains).

Prior to this invention, monoclonal antibody 5/6/3-B-3 had been used to quantify normal chondroitin-6-sulfated proteoglycans. This use of monoclonal antibody 5/6/3-B-3 requires that the tissue or sample be pretreated with chondroitinase or hyaluronidase thereby cleaving the glycosaminoglycan chains to leave shortened chains characterized by the 5/6/3-B-3 epitope. Caterson et al., "Monoclonal Antibodies As Probes For Elucidating Proteoglycan Structures and Function," In: Biology of Proteoglycans, ed., T. Wight and R. Mecham, pp. 1–26, Academic Press, N.Y. (1987). In contrast, it is an essential feature of the methods and compositions according to this invention that the antibodies are employed without pretreatment of the tissue or sample with enzymes that cleave the glycosaminoglycan chains to leave shortened chains or with enzymes or chemicals that remove the entire chain.

Monoclonal antibody 5/6/3-B-3 is available from ICN Biochemical in Cleveland, Ohio, or it may be prepared using Swarm rat chondrosarcoma proteoglycan core protein as antigen for immunization. A sample of monoclonal hybridoma 5/6/3-B-3 has been deposited at American Type Culture Collection, 12301 Parklawn Drive, Rockville, Md. 20852 on May 7, 1992 and has been assigned the accession number ATCC HB 11035. It is the preferred monoclonal antibody of this invention. Without wishing to be bound by theory, we believe that monoclonal 5/6/3-B-3 detects a terminal glucuronic acid residue adjacent to N-acetyl galactosamine-6-sulfate at the non-reducing end of chondroitin sulfate chains in proteoglycans.

Monoclonal antibody 8/25/7-D-4 can be produced using 17 day old embryonic chicken bone marrow proteoglycan as antigen. In contrast to monoclonal antibody 5/6/3-B-3, enzymatic (chondroitinase or hyaluronidase) cleavage of the chondroitin sulfate/dermatan sulfate chains to leave the shortened chains eliminates the epitope recognized by this antibody. While not wishing to be bound by theory, we believe that monoclonal antibody 8/25/7-D-4 detects an epitope of chondroitin sulfate/dermatan sulfate chains distinct from that of 5/6/3-B-3. However, the specific biochemical characteristics of this epitope have not yet been identified. A sample of monoclonal hybridoma 8/25/7-D-4 has been deposited at American Type Culture Collection, 12301 Parklawn Drive, Rockville, Md. 20852 on Jun. 20, 1991 and has been assigned the accession number ATCC HB 10173.

Other antibodies of this invention that are diagnostic for early stages of osteoarthritis are preferably prepared as described above using proteoglycans of cartilage extracts from a mammal suffering from osteoarthritis as an antigen in standard (conventional) immunization procedures as described in Caterson et al., "Monoclonal Antibodies As Probes For Elucidating Proteoglycan Structures and Function," In: Biology of Proteoglycans, ed., T. Wight and R. Mecham, pp. 1–26, Academic Press, N.Y. (1987). The antibodies of this invention are then selected by screening the collection of monoclonals produced against these antigens for those (1) that selectively recognize proteoglycans of cartilage extracts from a mammal suffering from osteoarthritis (preferably the same mammal from which the antigen used to raise the antibody is derived), (2) that do not recognize proteoglycans of cartilage extracts from a mammal not suffering from osteoarthritis (preferably the same mammal as used in the first screening and more preferably the same mammal as used to derive the antigen and in the first screening) and (3) that do not recognize proteoglycans of cartilage extracts from a mammal suffering from osteoarthritis, from which the chondroitin sulfate/dermatan sulfate chains have been completely removed by enzymatic or chemical treatment (again most preferably the same mammal from which the antigen used raising the antibody is derived and the same mammal used in the first and second screening).

According to the methods of this invention, the antibodies of the invention may be used to diagnose osteoarthritis in mammals using cartilaginous tissue, synovial fluid or serum. However, because the atypical chondroitin sulfate/dermatan sulfate chains that we have discovered as characteristic markers for this disease are present in equilibrium throughout the body, they may be found in other body tissues and fluids as well, e.g., urine.

The above described compositions are useful in various assays to diagnose or monitor the course of osteoarthritis. The fundamentals of such assays are well known and conventional in the art. They are useful in the various embodiments of this invention because of the specificities of the monoclonal antibodies of this invention that characterize them.

The diagnostic assays of this invention depend on the detection of an increased amount of atypical chondroitin sulfate/dermatan sulfate chains in a body fluid or tissue analyte. As used in this application, an increased amount is at least 2 fold over normal tissue or fluid. Most usually, the increased amount is between 2 and 150 fold. And more preferably, the increased amount is between 2 and 15 fold.

When the compositions of this invention are used to monitor the progression of osteoarthritis or the effect or course of therapy, the assays depend on following the presence and amount of the atypical chondroitin sulfate/dermatan sulfate chains in a body fluid or tissue analyte. In this embodiment of the invention, the relative amount of such chains is compared with that of normal tissue or body fluid and diseased tissue or body fluid samples before treatment or earlier in time to determine the course of disease or treatment.

One such assay, by way of example, is a radioimmunoassay as described by Ratcliffe and Hardingham, "Cartilage Proteoglycan Binding Region and Link Protein," *Biochem J.*, 213, pp. 371–78 (1983). In this particular assay system, synovial fluid samples may be analyzed in a competitive radioimmunoassay using $^{125}$I-labelled proteoglycans containing the epitope specifically recognized by the monoclonal antibody of this invention as labelled antigen, with heat denatured, formalin fixed *S. aureus* as an immunoprecipitant. We may then quantitate the results by calibration with a standard proteoglycan antigen. In the preferred embodiment of this invention, where 5/6/3-B-3 is the monoclonal antibody, human articular cartilage proteoglycans pretreated with chondroitinase would be radiolabelled. For assays using monoclonal antibody 8/25/7-D-4, 17-day old embryonic chicken bone marrow proteoglycans would be radiolabelled.

An alternative assay to diagnose osteoarthritis is characterized by the electrophoresis of samples of cartilage extracts on composite agarose/acrylamide slab gels. The extracts of cartilage and composite agarose/acrylamide gels may be, for example, prepared according to the method of Carney et al., "Electrophoresis of $^{35}$S-Labeled Proteoglycans on Polyacrylamide-Agarose Composite Gels and Their Visualization by Fluorography," *Analyt. Biochem*, 156, pp. 38–44 (1986), with a composite gel mixture of 1.2% (w/v) polyacrylamide and 0.6% (w/v) agarose. After electrophoresis, the proteoglycans are electrophoretically transferred onto nylon sheets and the occurrence of the osteoarthritis markers of this invention are detected by immunolocalization with the monoclonal antibodies of this invention, e.g., 5/6/3-B-3 or 8/25/7-D-4, using a peroxidase-conjugated second antibody for detection.

It should be noted that a variety of other assays such as an enzyme-linked immunosorbent assay (ELISA) and immunoradiometric assays may be employed as alternative methods of this invention using the antibodies of this invention.

Because we have for the first time discovered atypical structures that serve as markers for osteoarthritis, other conventional biochemical techniques, such as HPLC analysis or GC-Mass Spectrometry analysis may also be used to detect these atypical structures and thus to diagnose osteoarthritis or to monitor the course of the disease or therapy against it. For example, these atypical structures could be detected after conventional chemical or enzymatic cleavage of the glycosaminoglycan chains, fractionation of the resultant oligosaccharides by HPLC gel filtration and/or ion exchange methods, and chemical analysis using GC-Mass Spectrometry or other analytical procedures.

Another embodiment of this invention provides a therapeutic method and compositions in which the monoclonal antibodies of this invention may be linked to a pharmaceutical drug and administered directly in a pharmaceutically acceptable manner to osteoarthritic lesions. The preferred drug depends on the intended mode of therapeutic application. For example, such a drug might include cellular growth factors, cellular toxins, analogues of cytokine receptors or inhibitors of extracellular proteinases. The dosage and treatment regimens will depend upon factors such as the patient's health status, and the judgment of the treating physician.

In order that this invention may be better understood, the following examples are set forth. These examples are for the purpose of illustration only, and are not to be construed as limiting the scope of the invention in any manner.

EXAMPLE 1

A. Preparation of Antigen, Immunization and Cell Hybridization

Monoclonal antibody 5/6/3-B-3 was produced using Swarm rat chondrosarcoma proteoglycan core protein as antigen for immunization. The proteoglycan core protein was obtained after digestion of the proteoglycan monomer, A1D1 fraction, with chondroitinase ABC using the conditions described by Christner et al., *J. Biol. Chem.*, 255, 7102–05 (1980). Proteoglycan monomer A1D1 was isolated from Swarm rat chondrosarcoma as described by Baker and Caterson, *J. Biol. Chem.*, 254, 2387–2393 (1979). To prepare protein cores, A1D1 preparations (10 mg of A1D1/ml of buffer) were digested with chondroitinase ABC in 0.1M sodium acetate, 0.1M Tris-HCl, pH 7.3, at 37° C. with 0.01 units of enzyme/mg of A1D1. The reactions were complete in 4–8 hours as judged by measuring the absorbance of the reaction mixture at 232 nm (Saito et al., *J. Biol. Chem.*, 243, 1536–1542 (1968)). The reaction products were separated from the enzyme by chromatography on a Sepharose CL-6B column (1.5×140 cm) eluted with 0.15M $Na_2SO_4$; the protein cores eluted shortly after the void volume while the enzyme and the released oligosaccharides eluted later in more included positions. The protein cores used for immunization were purified by affinity chromatography on immobilized hyaluronic acid as described by Christner et al., *Anal. Biochem.*, 90, 22–32 (1978). Monoclonal antibody 8/25/7-D-4 was produced using 17 day old embryonic chicken bone marrow proteoglycan as antigen. The marrow proteoglycan monomer preparation was prepared as described by Sorrell et al., *Cell Tissue Res.*, 252, 523–31 (1988). Femora and tibiae were removed from cold-anesthetized 17-day white Leghorn chick embryos and stripped of soft tissue. The epiphyseal cartilages were removed and bones cut in half lengthwise. Marrow was scraped directly from bones into cold 4M guanidine HCl containing protease inhibitors (Sajdera and Hascall, *J. Biol. Chem.*, 244, 77–87 (1969)). After all bone marrow had been removed, excess 4M guanidine HCl was added so that the final volume was at least 20 times that of the bone marrow. This material was stirred continuously for 24 hours at 4° C. Samples were centrifuged at 15000×g for 30 minutes and the supernatant was collected. Solid CsCl was added to give a density of 1.5 gm/ml. After centrifugation at 100,000×g for 48 hours at 10° C., the bottom, middle and top thirds were carefully collected so as to prevent mixing of the fractions. Each fraction was dialyzed exhaustively, first against $H_2O$, then against 0.15M NaCl. Stock solutions of each antigen (800 µg/ml in sterile Dulbecco's phosphate-buffered saline, 5×0.5 ml aliquots) was prepared and stored at −20° C.

Female Balb/cJ mice (Jackson Laboratories; 4–8 weeks old) were immunized using as antigen either Swarm rat chondrosarcoma proteoglycan core protein (800 µg/ml) for the monoclonal antibody 5/6/3-B-3 or 17 day old embryonic chicken bone marrow proteoglycan monomer (400 µg/ml) for the monoclonal antibody 8/25/7-D-4. The antigen was administered to the mouse at six injection sites (hind foot pads, lateral thoracic and inguinal regions) using a procedure described by Caterson et al., "Biology of Proteoglycans" In: Biology of the Extracellular Matrix, T. Wight and R. Mecham, ed., pp. 1–26, Academic Press, N.Y. (1987). Injections were administered on days 1, 3, 6, 9 and 12 of the injection regimen. For the first injection (day 1) the antigen was mixed 1:1 with Freund's complete adjuvant, the second injection (day 3), Freund's incomplete adjuvant and the subsequent three injections (days 6, 9 and 12) with isotonic saline (0.15M NaCl). Approximately 50 µl of the antigen mixture was injected into each of the six injection sites of the mouse on each injection day. Hybridoma fusion was performed 2 days after the last injection (day 14).

Draining lymph nodes (axillary, brachial, inguinal, and popliteal lymph nodes) from the regions nearest the sites of injection on the mouse were dissected aseptically under a laminar flow hood and used as the source of proliferating lymphocytes for hybridoma production. Lymphocytes were dispersed by teasing the lymph nodes with forceps in a 25 mm Petri dish containing 2 ml sterile Dulbecco's phosphate-buffered saline and finally by repeated suction and aspiration through an 18 gauge needle using a 3 ml syringe. The lymphocytes were separated from adhering connective tissue by passing the cell suspension through a sterile glass wool filter plug in a Pasteur pipette and the cells washed twice with 40 ml of culture medium RPMI 1640 (Flow Laboratories) at 4° C.

Cell fusion was carried out according to the procedure developed by Kohler and Milstein. Approximately $1 \times 10^8$ lymphocytes were fused with $5 \times 10^7$ x63-Ag8.653 myeloma cells (a gift from Dr. John F. Kearney, University of Alabama at Birmingham, ATCC #CLR 1580) by dropwise addition of 1.5 ml of a fusion medium comprising 20% polyethylene glycol (PEG 4000, Fisher Scientific) and 5% dimethylsulfoxide in RPMI 1640 medium (Flow Laboratories).

B. Selection and Growth of Hybridoma

After cell fusion, cells were cultured in HAT medium (hypoxanthine, aminopterin, and thymidine at 37° C. with 5% $CO_2$ in a humid atmosphere. Ten to fourteen days later, 0.5 ml samples of medium from cultures containing hybridomas were taken and analyzed for antibodies recognizing epitopes present on the original proteoglycan antigen using ELISA and radioimmunoassay procedures described by Caterson et al., *J. Biol. Chem.*, 258, pp. 8848–54 (1983). Hybridoma cultures containing antibodies reacting specifically with epitopes present on the injected antigen were selected and cloned. Subsequently, the clones were transferred intraperitoneally by injecting $1 \times 10^7$ cells of a given clone (in 1.0 ml volume in Dulbecco's phosphate-buffered saline) into retired breeder Balb/cJ mice primed with 2, 6, 10, 14-tetramethylpentadecane (Aldrich Chemical Company). The malignant ascites fluid from these mice were then used to characterize the antibody specificity. Both of the subject hybrid antibodies 5/6/3-B-3 and 8/25/7-D-4 were demonstrated by standard techniques to be of IgM subclass. Monoclonal antibody 5/6/3-B-3 was also found to bind *S. aureus* protein A, an unusual property for the mouse IgM subclass.

C. Characterization of Monoclonal Antibody Specificity

Monoclonal antibody 5/6/3-B-3 was produced with chondroitinase ABC-treated Swarm rat chondrosarcoma proteoglycan monomer as an antigen. The antigenic specificity of 5/6/3-B-3 was defined using normal cartilage proteoglycans pretreated with either chondroitinase ABC, AC11 or mammalian hyaluronidase. J.

R. Couchman et al., Nature, 307, pp. 650-52 (1984); B. Caterson et al., "Monoclonal Antibodies As Probes For Elucidating Proteoglycan Structure And Function," In: Biology Of The Extracellular Matrix, ed. T. Wight and R. Mecham, Academic Press, pp. 1-26 (1987). This pretreatment shortens chondroitin sulfate chains and increases the amount of a non-reducing terminal glucuronic acid residue adjacent to a 6-sulfated N-acetylgalactosamine residue. This epitope is recognized by monoclonal antibody 5/6/3-B-3. These non-reducing terminal structures containing the 5/6/3-B-3 epitope are present in chondroitin sulfate chains in osteoarthritic human and dog cartilage proteoglycans (without prior chondroitinase or hyaluronidase pretreatment) but this epitope is found to a significantly lesser degree in normal or control tissues.

Monoclonal antibody 8/25/7-D-4 was produced using 17 day old embryonic chicken bone marrow proteoglycan as antigen. In this case, nonchondroitinase treated proteoglycan was used as the antigen. Characterization of the specificity of this monoclonal antibody indicated that the 8/25/7-D-4 epitope is only present in proteoglycans that have not had their chondroitin sulfate chains extensively cleaved by chondroitinase pretreatment. Exhaustive chondroitinase digestion removes the antigenic determinant recognized by 8/25/7-D-4 antibody indicating that the epitope resides in the chondroitin sulfate glycosaminoglycan chain. Thus the 8/25/7-D-4 epitope is a component structure of the intact chondroitin sulfate glycosaminoglycan chain.

EXAMPLE 2

Detection of Atypical Chondroitin Sulfate/Dermatan Sulfate Structures in Synovial Fluid from Joints by Radioimmunoassay Using Monoclonal 5/6/3-B-3

We induced experimental osteoarthritis in six mature (3-6 year old) Beagle dogs, using the method described by M. Pond and G. Nuki, "Experimentally-induced Osteoarthritis in the Dog," Ann. Rheum. Dis., 32, pp. 387-88 (1973). Three months after surgery, the animals were sacrificed and we injected 5 ml of sterile saline into the knee joints of the dogs. The contralateral knee joint serves as a control in our animal model. The joints were extended and flexed several times and the synovial fluid was then aspirated to dryness. We next prepared radiolabelled antigen containing 5/6/3-B-3 epitopes for standardization of our radioimmunoassay ("RIA") by $^{125}$I-iodination of chondroitinase ABC digested proteoglycans isolated from human articular cartilage. A. Ratcliffe and T. E. Hardingham, Biochem J., 213, pp. 371-78 (1983). In order to prepare the standard "unlabeled" antigen for measuring the epitope recognized by monoclonal antibody 5/6/3-B-3, we pretreated proteoglycans isolated from human articular cartilage with chondroitinase ABC. This pretreatment shortens the glycosaminoglycan chain(s) and creates many new carbohydrate chain termini containing the epitope recognized by 5/6/3-B-3. The $^{125}$I radiolabelled standardization antigen showed an appropriate titration with the 5/6/3-B-3 antibody and was used as the labelled antigen in competitive RIA analyses.

All of the test samples of synovial fluid obtained from either osteoarthritic or control dogs were analyzed without prior chondroitinase digestion so that only the amount of in vivo occurring 5/6/3-B-3 epitope on the chondroitin sulfate/dermatan sulfate chains was detected. Serial dilutions, using incubation buffer (0.15M NaCl, 0.01M Na$_2$HPO$_4$, pH 7.4 containing 0.5% (w/v) sodium deoxycholate, 0.1% (w/v) Nonidet P-40 and 0.1% (w/v) Bovine Serum Albumin), were prepared from each aspirate followed by competitive radioimmunoassay analysis. A dilution of the 5/6/3-B-3 antibody (100 µl) (sufficient to precipitate 50% of the $^{125}$I-labeled RIA standardization antigen) was mixed with dilute osteoarthritic samples or controls (50 µl) in incubation buffer together with $^{125}$I-labelled chondroitinase ABC digested human cartilage proteoglycan (20,000 dpm) in 1.5 ml plastic microcentrifuge tubes and incubated overnight at 20° C. A suspension (10% w/v) of S. aureus (30 µl) (heat denatured and formalin treated) was added and after mixing for 25 minutes the tubes were spun and the pellet washed twice with incubation buffer. The pellet and the combined supernatant and washings were next counted separately in a gamma radiation counter (LKB, Sweden). The inhibition of $^{125}$I-antigen binding achieved by the samples was compared with a set of standards of known antigen concentration and the results were expressed in units of concentration of the antigen (chondroitinase digested human proteoglycan).

Table 1 compares the level of monoclonal antibody 5/6/3-B-3 epitope between normal (synovial fluid from contralateral control joint) and osteoarthritic ("OA") joints. In each case, the presence of increased amounts of 5/6/3-B-3 epitope in the synovial fluid from the osteoarthritic joints was demonstrated.

TABLE 1

| Radioimmunoassay of 5/6/3-B-3 in Synovial Fluid from Joints with Experimental Osteoarthritis | | |
|---|---|---|
| Dog No. | Joint | Antigen ng/ml |
| 74 | normal | <0.5 |
|  | OA | 4.4 |
| 75 | normal | 1.0 |
|  | OA | 2.0 |
| 76 | normal | <0.5 |
|  | OA | 5.7 |
| 77 | normal | <0.5 |
|  | OA | 69.0 |
| 558 | normal | 1.0 |
|  | OA | 142.0 |
| 562 | normal | 5.0 |
|  | OA | 36.0 |

EXAMPLE 3

Detection of Atypical Chondroitin Sulfate/Dermatan Sulfate Structures In Cartilage Proteoglycans from Joints Using Monoclonal Antibodies 5/6/3-B-3 and 8/25/7-D-4

We induced experimental osteoarthritis in dogs as described by Pond and Nuki. Cartilage was freshly dissected from tibial plateau, patellar groove and femoral condyles 3 months after ligament section and was extracted in 10 volumes of 4M guanidine HCl, 0.5M sodium acetate pH 5.8 containing proteinase inhibitors (0.1M 6-aminohexanoic acid, 0.01M disodium ethylene diamine tetracetic acid, benzamidine HCl and 0.001M phenyl-methanesulphonylfluoride). The extract was dialyzed against several changes of 8M urea and the proteoglycan concentration was determined in a dye binding assay described by R. W. Farndale et al., Conn. Tiss. Res. 9, pp. 247-48 (1982). We used cartilage from the contralateral unoperated joint as a control.

Proteoglycans extracted from the cartilage from different joint regions were next compared by electrophoresis on composite agarose/acrylamide slab gels. The gels were prepared by suspending agarose (0.24 g) in 22 ml gel buffer (0.04M Tris-acetate/1 mM Na$_2$SO$_4$ pH 6.8) and heating to 90° C. Acrylamide (0.456 g) and bisacrylamide (0.024 g) were dissolved in gel buffer (9.7 ml) and beta-dimethylaminoproprionitrile (0.4% w/v; 4.8 ml) was added to it and the mixture was warmed. The agarose solution was allowed to cool to 52° C. and ammonium persulfate (0.3% v/v; 3 ml) was added to the acrylamide solution, followed by mixing thoroughly with the agarose and quickly poured into the gel cast, which was preheated to 50° C. (A plug of acrylamide (10% w/v) of depth 50 mm was preformed in the bottom of the gel support in order to hold the composite gel in place during electrophoresis.) Water saturated n-butanol was layered on top of the freshly poured gel to exclude air during polymerization. The gel was placed in the cold (4° C.) for 1 hour and then equilibrated in buffer containing 4M urea overnight. Samples containing about 10 μg proteoglycan in buffer (0.01M Tris-acetate/0.25 mM Na$_2$SO$_4$ containing 8M urea and 0.001% (w/v) bromophenol blue, pH 6.8) were loaded in each track. Gels were electrophoresed at 4° C. initially at 60 V until the bromophenol blue had entered the gel and then at 120 V until it had migrated 30 mm. Replicate gels were run in this manner. One gel was then stained with toluidine blue (0.2% (w/v) in 0.1M acetic acid to reveal proteoglycan bands and replicate gels were left unstained for electroblotting.

Electrophoretic transfer to a nylon sheet (Gelman Biotrace RP) was carried out with minimal amounts of buffer (0.01M Tris-acetate, 0.25 mM Na$_2$SO$_4$ pH 6.8) in a semi-dry electroblotter (Sartorius, Belmont, UK) run at 80 mA for one hour. The nylon sheet was rinsed with water and dried on filter paper. For immunolocalization of atypical chondroitin sulfate/dermatan sulfate chains, the method used was essentially that of A. L. Deblas and H. M. Cherwinski, *Analyt. Biochem.*, 133, pp. 214–219 (1983), as described for nitrocellulose sheets. The nylon sheet was wetted in phosphate buffered saline (PBS) (0.14M NaCl, 0.01M Na$_2$HPO$_4$, pH 7.4) and protein absorptive sites were blocked by incubation with 1% (w/v) bovine serum albumin (BSA) in PBS for 1 hour. The sheet was then incubated in antibody 5/6/3-B-3 or 8/25/7-D-4 (1 in 1000 dilution in PBS) for 1.5 hours and then washed for 5 minutes in six changes of PBS. It was then incubated with peroxidase-conjugated rabbit antimouse immunoglobulin (Sigma, St. Louis, Mo.) (1 in 1000 dilution in PBS containing 1% (w/v) BSA) for 1 hour followed by 5 minutes of washing in six changes of PBS. The sheet was then incubated with peroxidase substrate (diaminobenzidine/cobalt chloride/ammonium nickel sulfate reagent) for 15 minutes in the dark followed by fresh reagent, but also containing H$_2$O$_2$ to develop the staining (30–90 minutes). The atypical chondroitin/dermatan sulfate epitopes localized by the antibodies on the nylon sheet appeared as darkly stained bands on an unstained background. The distribution and intensity of the bands were recorded by preparing densitometric scans on a dual wavelength TLC scanner CS-930 (Shimadzu, Japan). This permitted quantitative comparison of OA and normal samples detected under identical conditions on the same nylon sheet.

Figure 1:
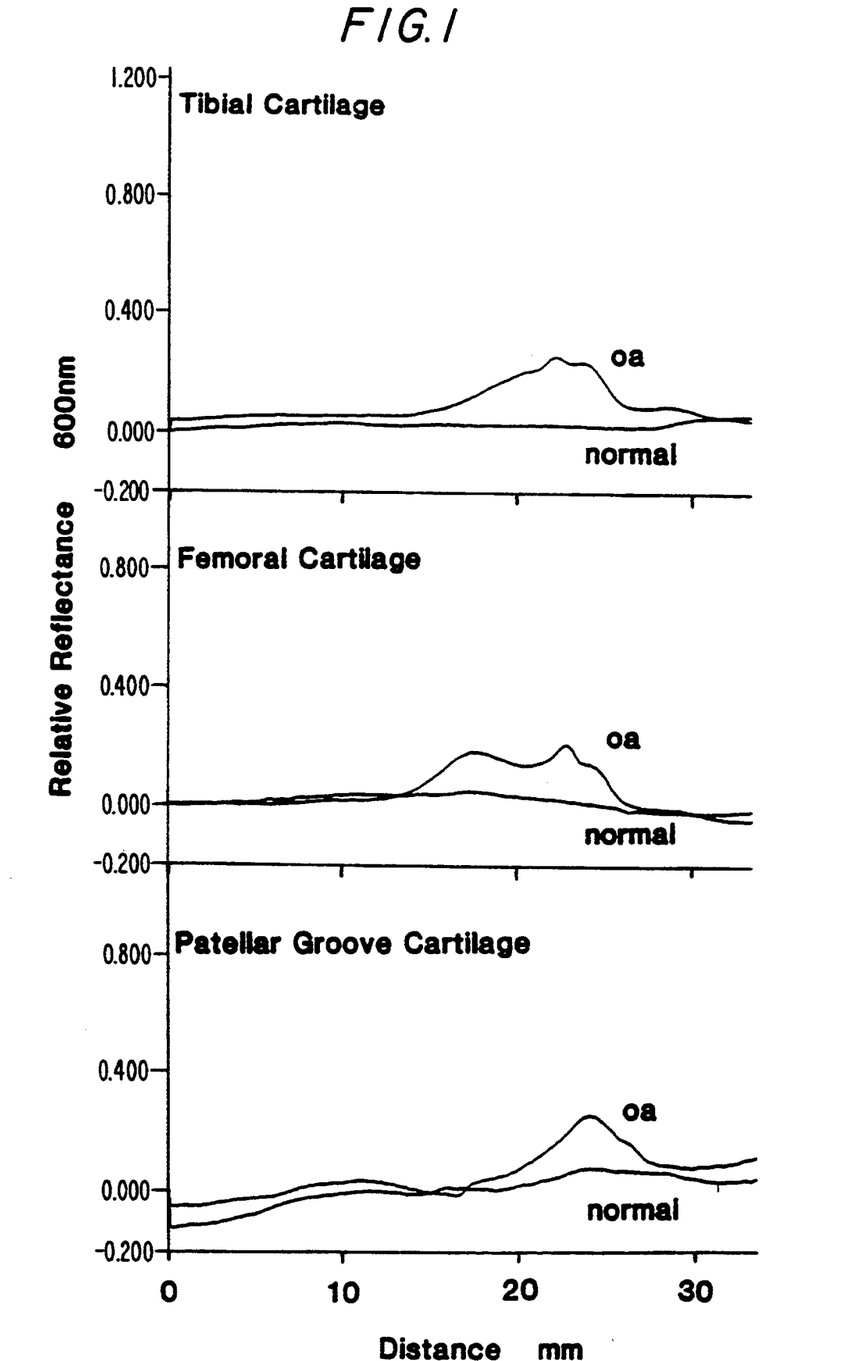
FIG. 1 depicts densitometric scans of 5/6/3-B-3 immunoblots of proteoglycans from tibial, femoral and patella groove cartilage from normal and osteoarthritic knee joints of mature dogs 3 months after experimental osteoarthritis was induced.

As shown in FIG. 1, expression of the atypical chondroitin sulfate/dermatan sulfate epitope recognized by monoclonal antibody 5/6/3-B-3 is increased in osteoarthritic cartilage from all areas 3 months after osteoarthritis was induced as compared to the contralateral control.

We also employed monoclonal antibody 8/25/7-D-4 in place of 5/6/3-B-3 using the same techniques described above. Similarly, FIG. 2 shows the atypical chondroitin sulfate/dermatan sulfate epitope recognized by 8/25/7-D-4 was expressed more strongly in proteoglycans in osteoarthritic cartilage compared with control joints.

Quantitative assessment of the immunoblotting from parallel tracks showed an average increase to 440% of control in the proteoglycans from osteoarthritic cartilage (see Table 2).

TABLE 2

Figure 2:
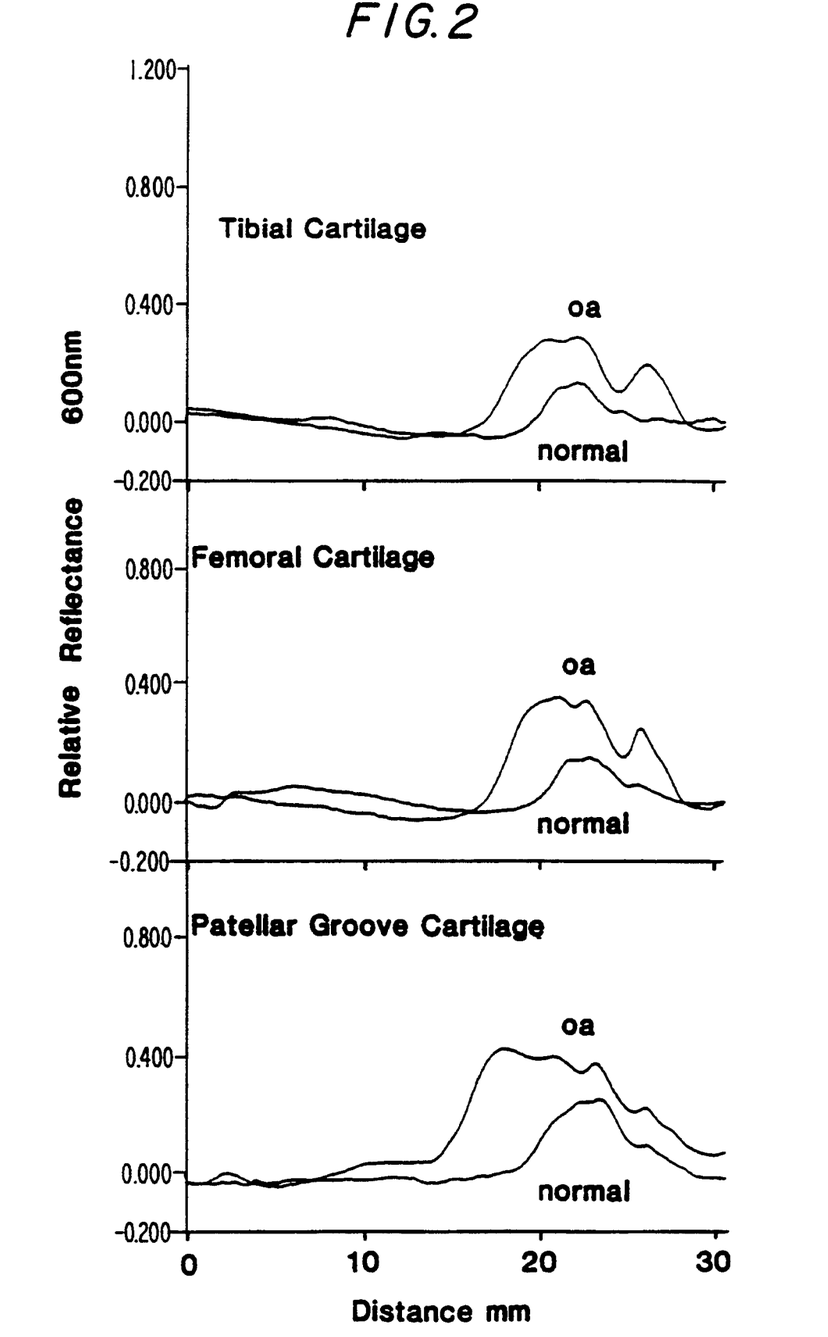
FIG. 2 depicts densitometric scans of 8/25/7-D-4 immunoblots of proteoglycan preparations from normal and osteoarthritic cartilage of mature dogs 3 months after experimental osteoarthritis was induced.

8/25/7-D-4 Epitope in Proteoglycans from Experimental Canine Osteoarthritis Analysis of Densitometric Scans (FIG. 2)

| Animal Number | Region | Epitope Abundance Expressed as % of control | Average |
|---|---|---|---|
| 74 | femoral | 428 | 327 |
|  | tibial | 348 |  |
|  | patellar | 204 |  |
| 75 | femoral | 348 | 305 |
|  | tibial | 359 |  |
|  | patellar | 208 |  |
| 77 | femoral | 475 | 688 |
|  | tibial | 1115 |  |
|  | patellar | 474 |  |

EXAMPLE 4

Figure 3A:
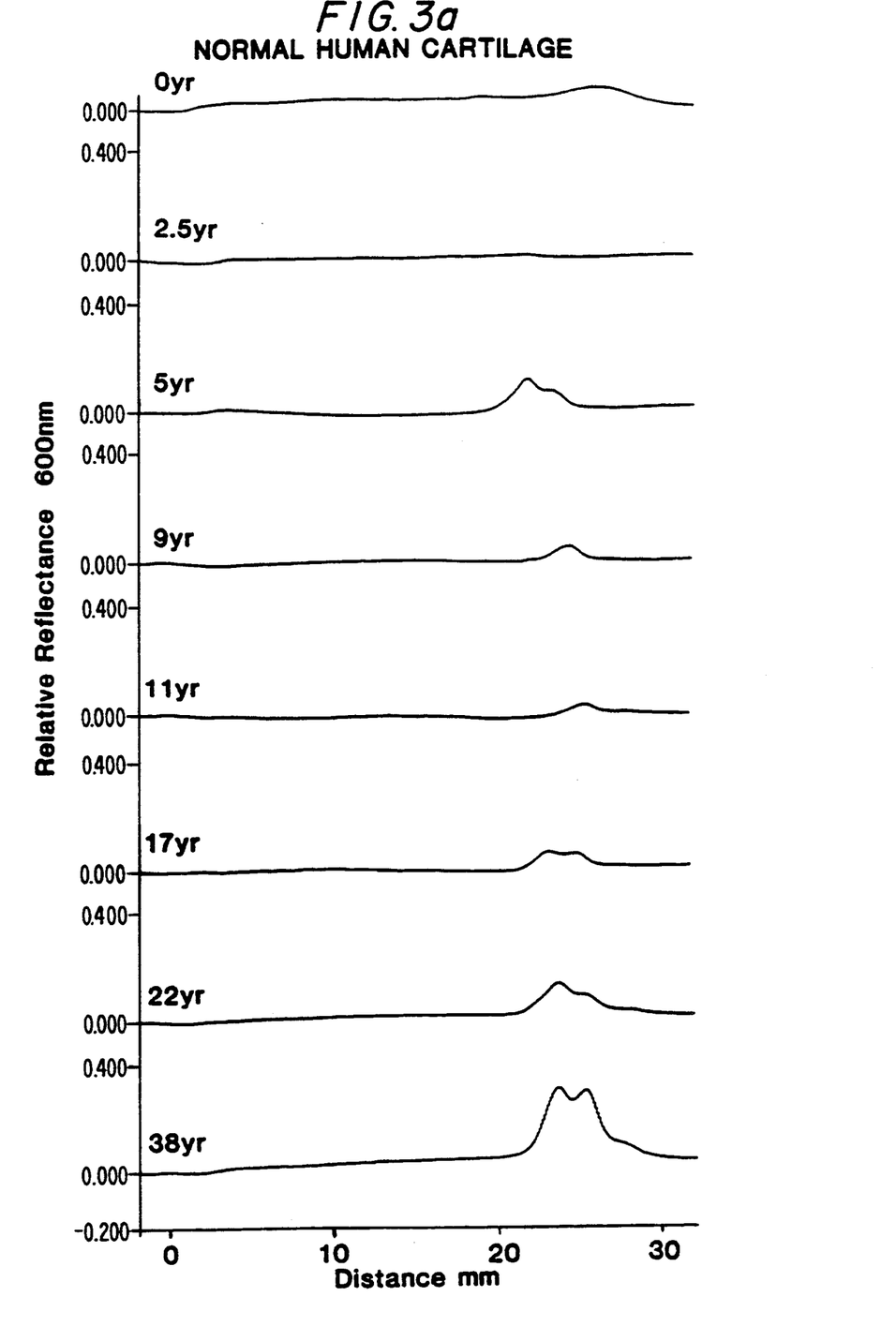
FIGS. 3a and 3b depict densitometric scans of 5/6/3-B-3 immunoblots of proteoglycans from normal human cartilage.
Figure 3B:
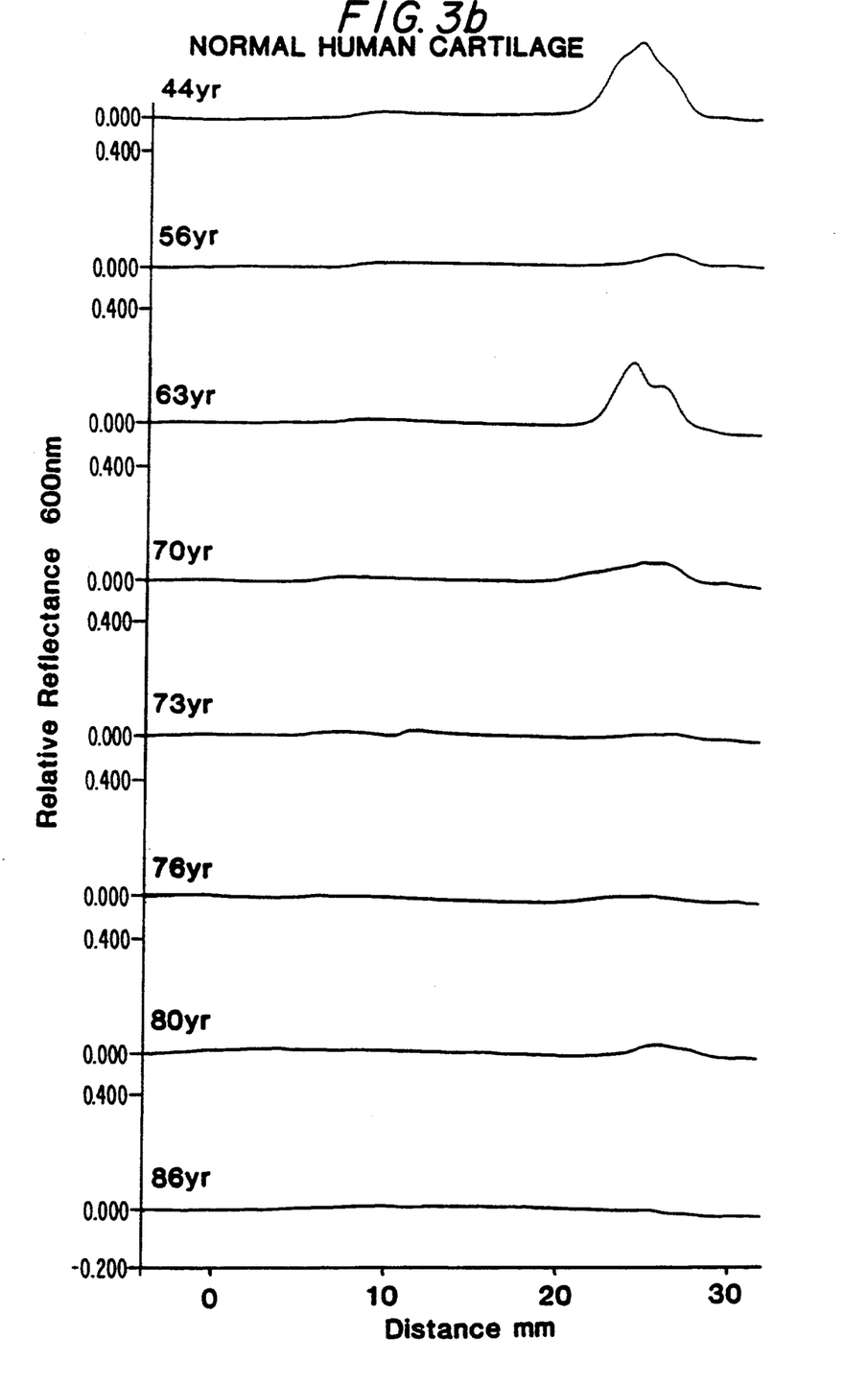
Figure 4A:
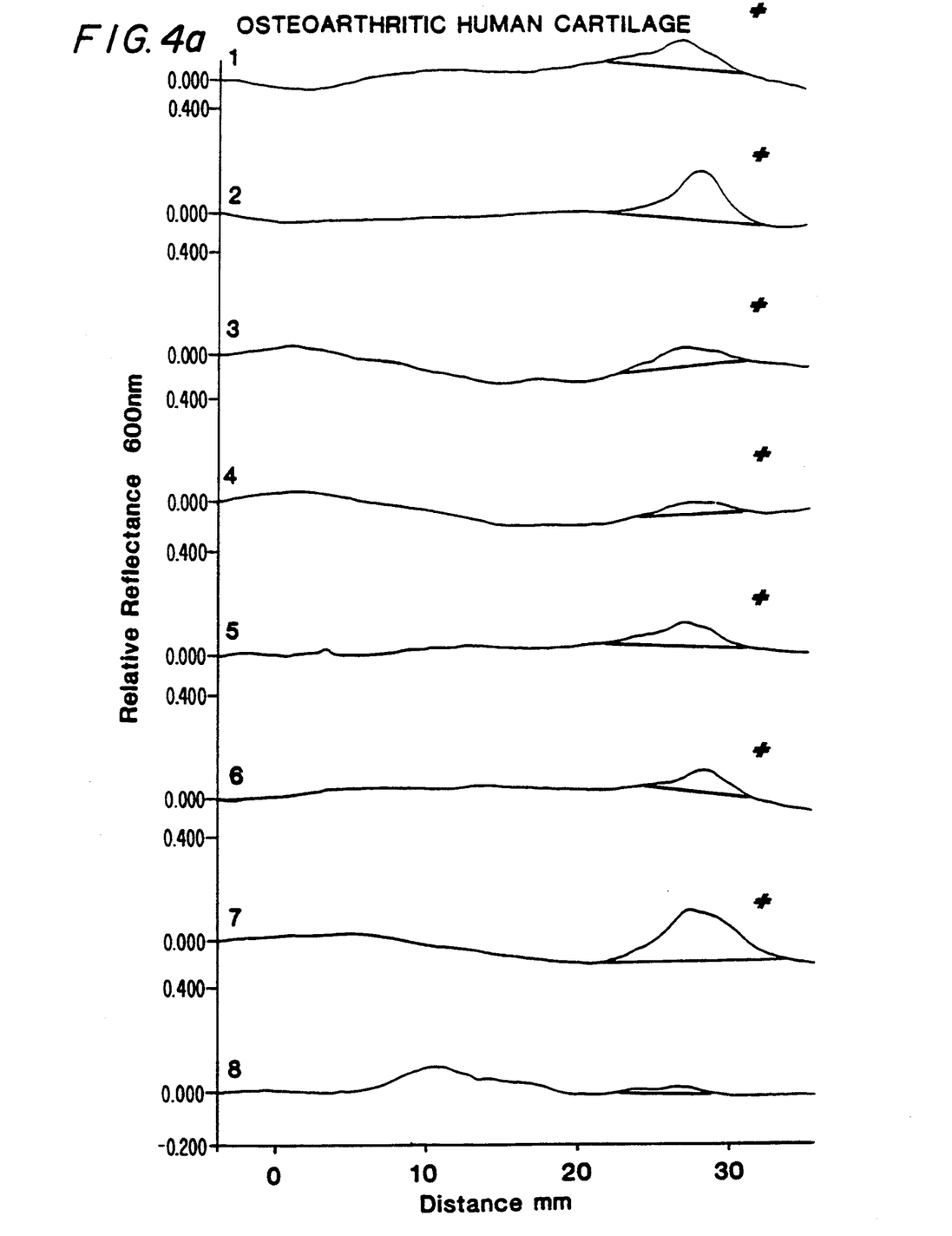
FIGS. 4a and 4b depict densitometric scans of 5/6/3-B-3 immunoblots of proteoglycans from osteoarthritic human cartilage.
Figure 4B:
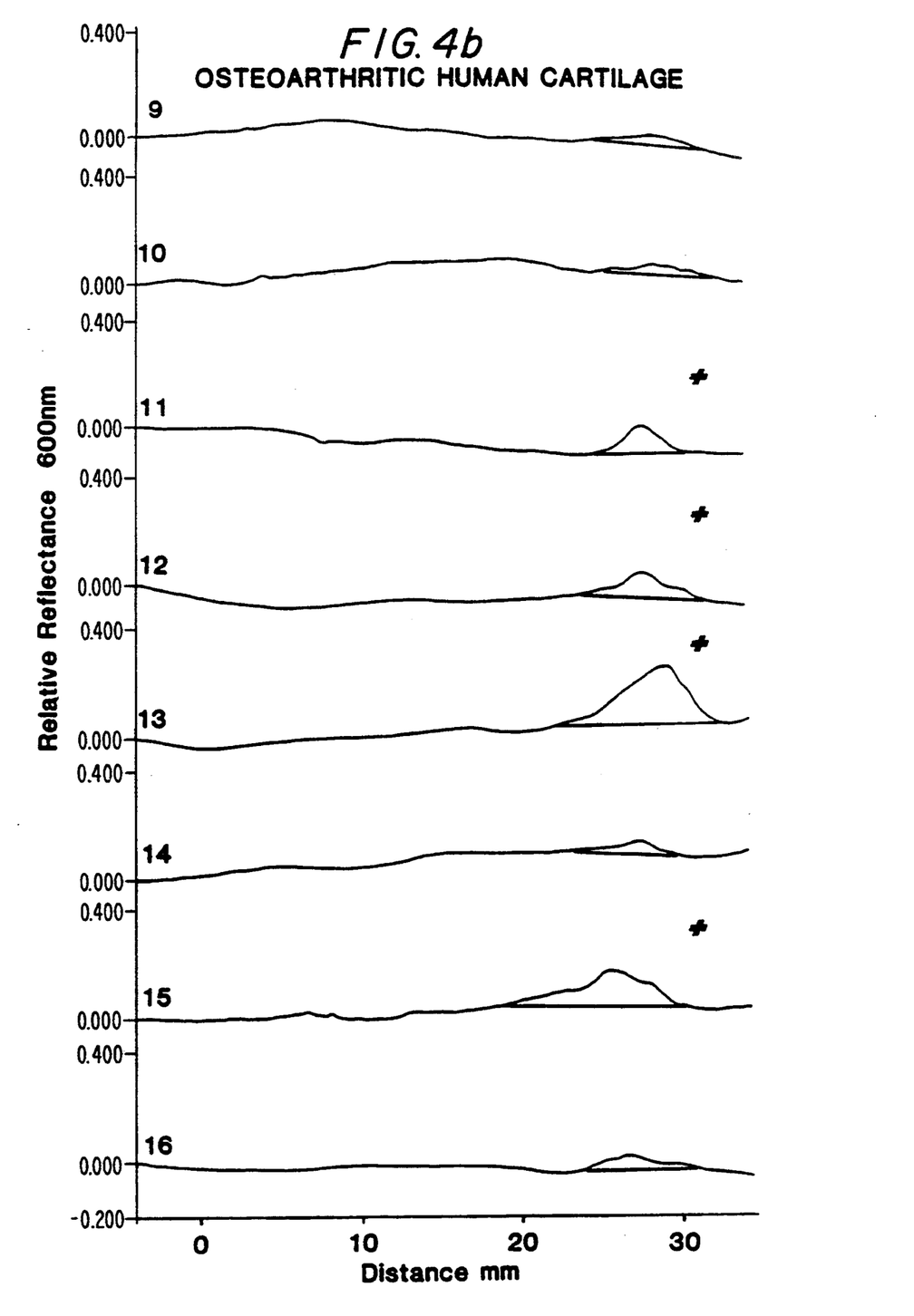

Detection of Atypical Chondroitin Sulfate/Dermatan Sulfate Chains in Osteoarthritic Human Articular Cartilage We obtained human cartilage samples from 16 osteoarthritic femoral heads removed at joint replacement (65–85 yrs) and 15 normal femoral head or femoral condyle specimens (0–80 yrs) and compared the presence of atypical chondroitin sulfate/dermatan sulfate chains using the same method described in Example 1, using monoclonal antibody 5/6/3-B-3, except for taking densitometric scans. We observed 11 out of 16 immunoblots of the proteoglycans in osteoarthritic samples (FIGS. 4a and 4b) and 3 out of 15 normal samples (FIGS. 3a and 3b) as being positive for the atypical chondroitin sulfate/dermatan sulfate recognized by 5/6/3-B-3. In the latter case, we believe that 2 of these 3 "normal" samples were positive because they were obtained from apparently normal cartilage adjacent to osteoarthritic lesions. This cartilage would be expected to contain atypical chondroitin sulfate/dermatan sulfate chains indicative of osteoarthritis. We found atypical chondroitin sulfate/dermatan sulfate chains were present at low levels in all other normal human samples.

It will be appreciated that the scope of this invention is to be defined by the claims appended hereto rather than by the specific embodiments which have been presented herein by way of example.

We claim:

1. A method for detection of osteoarthritis in a mammal comprising the steps of:
    a) reacting a body material selected from the group consisting of cartilaginous tissue, synovial fluid, serum and urine from a patient suspected of suffering from osteoarthritis, with a monoclonal antibody selected from the group consisting of monoclonal antibody 5/6/3-B-3 (ATCC HB 11035) and monoclonal antibodies that bind to the same epitope as monoclonal antibody 5/6/3-B-3;
    b) detecting at least a two fold difference in the amount of said monoclonal antibody that binds to chondroitin sulfate/dermatan sulfate glycosaminoglycan chains in the body material of said patient as compared to the amount of said monoclonal antibody that binds to chondroitin sulfate/dermatan sulfate glycosaminoglycan chains in the body material of a normal mammal as an indication of osteoarthritis.

* * * * *